United States Patent [19]

Lauks et al.

[11] Patent Number: 4,739,380

[45] Date of Patent: Apr. 19, 1988

[54] INTEGRATED AMBIENT SENSING DEVICES AND METHODS OF MANUFACTURE

[75] Inventors: Imants R. Lauks, Sewell, N.J.; Jan Van der Spiegel, Philadelphia, Pa.

[73] Assignee: Integrated Ionics, Inc., Dayton, N.J.

[21] Appl. No.: 572,185

[22] Filed: Jan. 19, 1984

[51] Int. Cl.⁴ .................... H01L 29/66; H01L 29/96
[52] U.S. Cl. ................................. 357/25; 357/22; 357/34; 357/40
[58] Field of Search .............. 357/22, 25, 22 B, 34, 357/23.15, 71, 40, 41; 174/102 R, 102 SC, 102 C, 102 SP; 33/160, 161; 156/661.1; 430/312, 316

[56] References Cited

U.S. PATENT DOCUMENTS

| | | | |
|---|---|---|---|
| 3,605,045 | 9/1971 | Ramsbotham, Jr. | 333/204 OR |
| 3,621,367 | 11/1971 | Rosen | 333/204 X |
| 4,238,757 | 12/1980 | Schenck | 357/25 |
| 4,251,621 | 2/1981 | Fraley et al. | 156/661.1 X |
| 4,332,658 | 6/1982 | Tsuboshima | 357/25 X |
| 4,508,613 | 4/1985 | Busta et al. | 357/25 X |

OTHER PUBLICATIONS

Barrett, R. M., "Etched Sheets Serve as Microwave Components", Electronics, Jun. 1952, pp. 114–118.

*Primary Examiner*—Andrew J. James
*Assistant Examiner*—Sara W. Crane
*Attorney, Agent, or Firm*—Pennie & Edmonds

[57] ABSTRACT

An ambient sensing device is described especially suited to the sensing of a variety of ambient parameters. Photolithographic techniques are used to pattern a multiplicity of sensitive layers on a single monolithic substrate taking into account the wide range of plastic, gelatinous and ceramic materials to be patterned and the problems of their cross-contamination when in contact.

8 Claims, 9 Drawing Sheets

INTEGRATED AMBIENT SENSING DEVICES AND METHODS OF MANUFACTURE

CROSS REFERENCE TO RELATED APPLICATIONS

Related applications are "Ambient Sensing Extended Gate Transistor," Ser. No. 572,182, now abandoned; "Ambient Sensing Devices," Ser. No. 572,199, now U.S. Pat. No. 4,613,422; "Method of Calibrating Conductive Metal Oxide Electrodes," Ser. No. 572,200, now U.S. Pat. No. 4,551,209; and "Ambient Sensing Devices Using Polyimide," Ser. No. 572,213, filed concurrently herewith, and "Amorphous Metal Oxide Electrodes," Ser. No. 441,902, filed Nov. 15, 1982, now abandoned in favor of Ser. No. 732,380, which are incorporated herein by reference.

BACKGROUND OF THE INVENTION

This relates to ambient sensing devices such as ion sensitive and chemical sensitive devices and to methods of manufacturing such devices that are especially suited to the manufacture of multi-element devices having sensitivity to different ions or chemicals.

It frequently is necessary to monitor the composition of a chemical environment, for example, to regulate chemical or biochemical processes, to determine air or water quality, or to measure parameters of interest in biomedical, agricultural or animal husbandry disciplines. One means of the detection, measurement and monitoring of the chemical properties of a substance involves the measurement of potential difference between two electrodes with the potential difference being dependent upon the chemical activity being measured. Because of the nature of the chemical environment, it is desirable that any measurement apparatus have at least some of the properties of: low cost, simple fabrication methodology, digital operation, some degree of signal preconditioning or intelligence, small size, high chemical sensitivity with selectivity, multiple species information with specificity, choice of reversible or integrating response to chemical species, temperature insensitivity or compensation and low power operation. In addition the measurement apparatus should have good long term electrochemical stability, good physical resiliency and strength and good resistance to corrosion and chemical attack. In the case of electrical measurement devices, the devices should also have low electrical impedance to provide good signal to noise ratios and preferably a Nernstian response to the chemical phenomena being measured.

Bergveld has proposed that hydrogen and sodium ion activities in an aqueous solution be measured by a metal oxide semiconductor field-effect transistor (MOSFET) modified by removal of the gate metal. P. Bergveld, "Development, Operation, and Application of the Ion-Sensitive Field-Effect Transistor as a Tool for Electrophysiology" *IEEE Transactions of Biomedical Engineering*, Vol. BME-19, pages 342-351 (September, 1972). In particular, if a MOSFET with no gate metal were placed in an aqueous solution, Bergveld suggested that the silicon dioxide insulation layer would become hydrated and then, because of impurities in the hydrated layer, ion selective. After hydration of the insulation layer of the MOSFET, Bergveld believed the device could be used for ion activity measurement by immersing the device in the solution in question and then recording conductivity changes of the device. Thus, the Bergveld device is commonly referred to as an ion-sensitive field effect transistor (ISFET).

Bergveld's work led to other developments in the field of ion sensitive electrodes such as the chemical sensitive field effect transistor (CHEMFET) device described in U.S. Pat. No. 4,020,830 which is incorporated herein by reference. As described in the '830 patent, the CHEMFET is a MOSFET in which the gate metal has been replaced by a chemically selective system that is adapted to interact with certain substances to which the system is exposed. Thus as shown in FIGS. 1 and 2 of the '830 patent, the CHEMFET is identical in structure to a MOSFET except for a membrane 38 that is deposited in place of a metal gate layer on the oxide insulator above the channel region of the transistor and, optionally, an impervious layer 44 that covers all other parts of the CHEMFET that might be exposed to the solution. Numerous variations on CHEMFET structures are disclosed, for example, in U.S. Pat. Nos. 4,180,771, 4,218,298, 4,232,326, 4,238,757, 4,305,802, 4,332,658, 4,354,308, 4,485,274 and 4,397,714. Further improvements in these structures are disclosed in application Ser. No. 441,902.

One continuing problem has been the need to provide multi-element probes. Study of chemical phenomena invariably requires more than one electrode. Even if only one parameter is being monitored by a single electrode, a reference electrode is also needed. However, because ionic concentrations are a function of pH, pH monitoring is also needed; and it is generally necessary to monitor for the presence of other ionic concentrations that might interfere with the measurement of primary interest. Because concentrations vary with space and time, it is also desirable to perform all measurements at the same time and as close together as possible. Despite the obvious need for measurements of multiple species and speculation about building such devices on monolithic structures as in S. Pace, "Surface Modification and Commercial Applications," *Sensors and Actuators*, Vol. 1, pp. 475 (1982), the technological difficulties associated with the marriage of different ion selective membrane materials and methods have to date thwarted any development of a significant multi-element technology. For example, no solution has been offered in the prior art for patterning a multiplicity of chemically sensitive materials such as plastics, gels and ceramics on one substrate without cross-contamination of the materials in contact. Although a two-specie probe has been described by M. Esaski et al., "Integrated Micro Multi Ion Sensor Using Field Effect of Semiconductor," *IEEE Trans. Biomed. Eng.*, Vol. BME-25, No. 2, pp. 184-192 (March 1978), this device uses the same technology as a single specie probe with one chemically sensitive layer being formed by standard photo-lithography and the other by dip coating from solution.

SUMMARY OF THE INVENTION

We have devised a method for forming multi-element probes on a single monolithic substrate such as a silicon planar device using photolithographic techniques to pattern the multiplicity of chemically sensitive layers taking into account the wide range of plastic, gelatinous and ceramic material to be patterned and the problems of their cross-contamination when in contact. In accordance with one aspect of our invention, two inorganic membranes sensitive to different chemical species may be deposited in vacuum on the same silicon substrate. In this technique, a photoresist is first formed on the silicon substrate. A window is then made in the photoresist for the formation of the first chemical sensitive layer. The substrate is then dipped in solvent to cause surface expansion of the photoresist and a first sensitive layer is then vacuum deposited on the substrate. The photoresist is then removed by a resist stripper, leaving bare the surface of the substrate except for the region on which the first sensitive layer was deposited. A second photoresist layer is then deposited and this layer is exposed and treated to form a window in the photoresist where a second sensitive layer can be formed. The photoresist is then dipped in solvent to expand its surface and the second sensitive layer is then applied by vacuum deposition. By treating the resist in a resist stripper, the second sensitive layer can be removed from all portions of the device except that portion that was deposited in the window in the photoresist. This process can be repeated indefinitely to form still additional sensitive layers on the surface of the substrate.

In a second embodiment of the invention, a PVC film containing valinomycin and a plasticizer is spin-coated on the substrate and is then overcoated with a thin inorganic material. This inorganic material serves to isolate the organic material from the photoresist that is subsequently used. A layer of photoresist is then deposited on the inorganic material and a pattern is defined photolithographically in the photoresist above a first region of the substrate. This pattern is then transferred by etching into the inorganic and PVC layers to form a first chemical sensitive device. After removal of the photoresist remaining above the inorganic material covering the first region, a second PVC layer can be deposited on the entire substrate including the inorganic material above the first region without substantially contacting or mixing with the already deposited PVC layer. This second layer is then coated with an inorganic material. Another layer of photoresist can then be deposited and shaped to form a second pattern on a second region of the substrate. This pattern can likewise be transferred to the inorganic material and the PVC layer by etching to form a second chemical sensitive device. Finally, the remaining photoresist can be removed and the process repeated indefinitely to form still other chemical sensitive devices. As a final step the inorganic capping layers are removed from all PVC layers.

This technique can be similarly utilized to pattern any kind of membrane deposited from a solution or from a solvent suspension. Therefore, gelatinous materials, heterogeneous polymer membranes or epoxies with entrapped aqueous electrolyte as described in a related application "Ambient Sensing Devices," Ser. No. 572,199, now U.S. Pat. No. 4,613,422, could be patterned accordingly.

With these techniques and/or modifications of conventional photolithographic techniques ambient sensitive devices can be formed on monolithic semiconductive substrates and these devices can be integrated into conventional signal processing circuitry. In addition, devices sensitive to a plurality of different chemical or ionic species can be fabricated on a single substrate.

The devices that can be made with these techniques encompass the range of potentiometric sensors presently available. In addition, the techniques can also be used to fabricate amperometric sensors such as an extended emitter bipolar transistor and an extended source junction field effect transistor.

BRIEF DESCRIPTION OF THE DRAWINGS

These and other objects, features and advantages of the invention will be more readily apparent from the following detailed description of preferred embodiments of the invention, which is provided by way of illustration, in which.

DESCRIPTION OF PREFERRED EMBODIMENT

Figure 1:
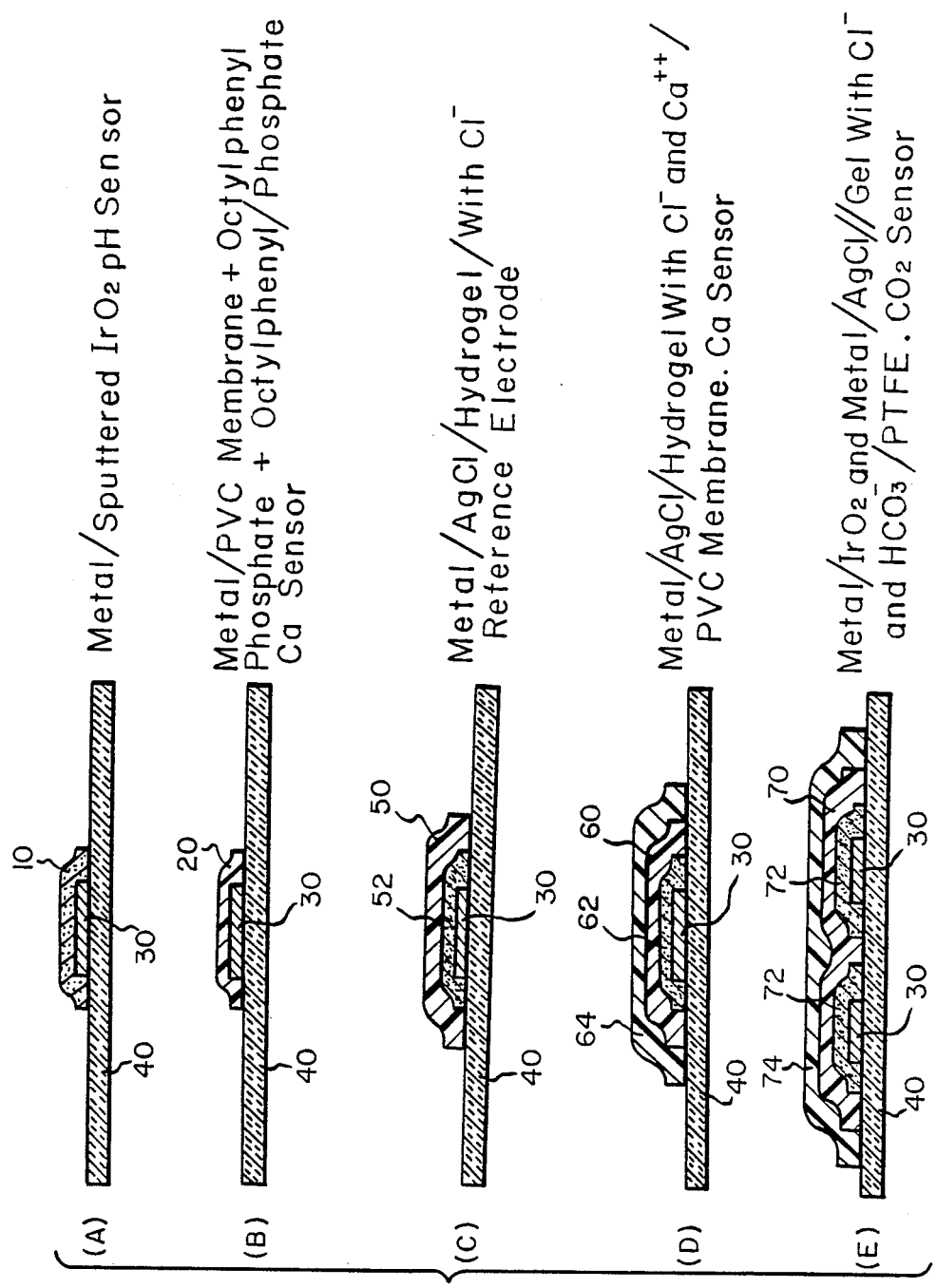
FIGS. 1A–1E are schematic representations of different types of chemical sensitive devices.

Typical prior art electrode structures are shown in FIGS. 1A–1E. The simplest structures of FIGS. 1A and 1B are obtained with a single coating step: vacuum or chemical vapor deposition of an inorganic layer 10 (e.g. $IrO_2$ for pH, AgCl for $Cl^-$, $Ag_2S$ for $S^-$, $LaF_3$ for $F^-$) or spin coating of ionophore doped polymer layer 20 (e.g. valinomycin doped PVC for $K^+$, octylphenylphosphate doped PVC for $Ca^{++}$) onto an electrical conductor 30 on a substrate 40. In cases where the inorganic layer is electrically conductive as with the platinum or rhenium metal oxides disclosed in application Ser. No. 441,902, a separate electrical conductor need not be used. The reference electrode structure of FIG. 1C consists of an electrolyte gel 50 containing $Cl^-$ over an AgCl layer 52 vacuum coated on conductor 30. The electrode structure depicted in FIG. 1D has an internal reference half cell consisting of gel 60 containing $Cl^-$ and the ion to be sensed, over an AgCl layer 62 coated on the substrate conductor 30. An ion sensitive membrane 64 would typically be spin coated ionophore doped organic polymer, although some vacuum coatings may also be feasible. The most complex structure shown in FIG. 1E is the electrochemical gas sensor or enzyme sensor, requiring sequential deposition of gel 70 and polymer 74 over a pair of ion sensitive electrodes each of which is formed of an inorganic layer 72 deposited on a conductor 30.

Figure 2:
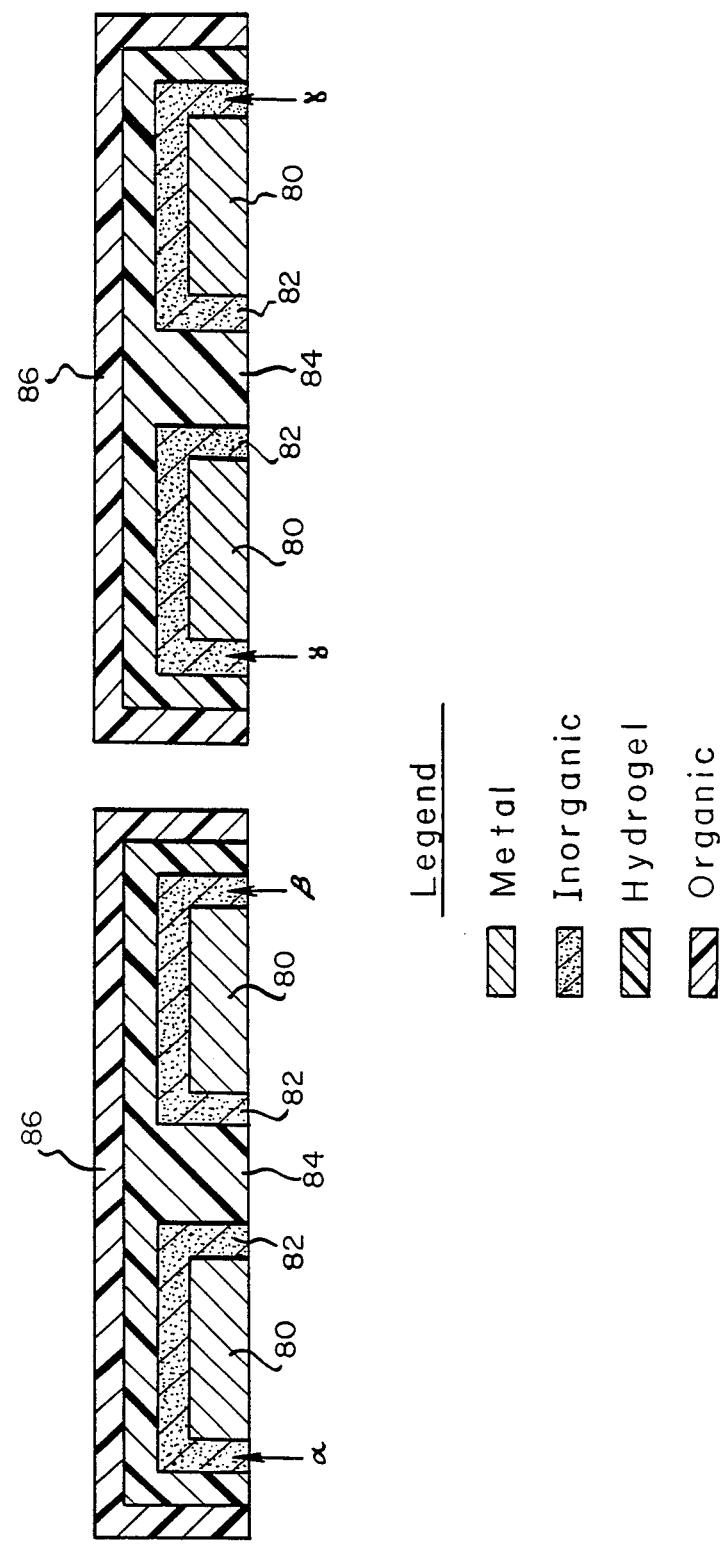
FIG. 2 is a schematic representation of a multi-element electrode.

As an example of the complexity of the planar microfabrication of even the smallest of chemically sensitive device arrays, consider a structure consisting of a pair of electrochemical enzyme or gas sensors. Such a structure is shown in cross section in FIG. 2. The structure of these electrodes is similar comprising an innermost layer 80 of metal coated with an inorganic layer 82 which is coated with a hydrogel 84 that in turn is covered with an organic layer 86. For instance the electrode on the left could be a $CO_2$ sensor consisting of an electrode pair—$IrO_x$ coated metal reversible to $H^+$ and AgCl coated metal reversible to $Cl^-$, overcoated with a quasi-solid electrolyte consisting of aqueous NaCl +$NaHCO_3$ immobilized in acrylamide gel topped with a $CO_2$ permeable polytetrafluoruethylene (PTFE) film. The electrode on the right might be a $H_2S$ sensor consisting of $Ag_2S$ and AgCl coated metals, pH buffered NaCl gel, and PTFE. The lithographic processing required for the fabrication involves four mask levels. The first, patterning of the metal, is straighforward. The second mask level requires the patterning of different vacuum deposited materials side-by-side. Similarly, the third and fourth mask levels require side-by-side patterning of gels and polymers of different compositions.

Figure 3:
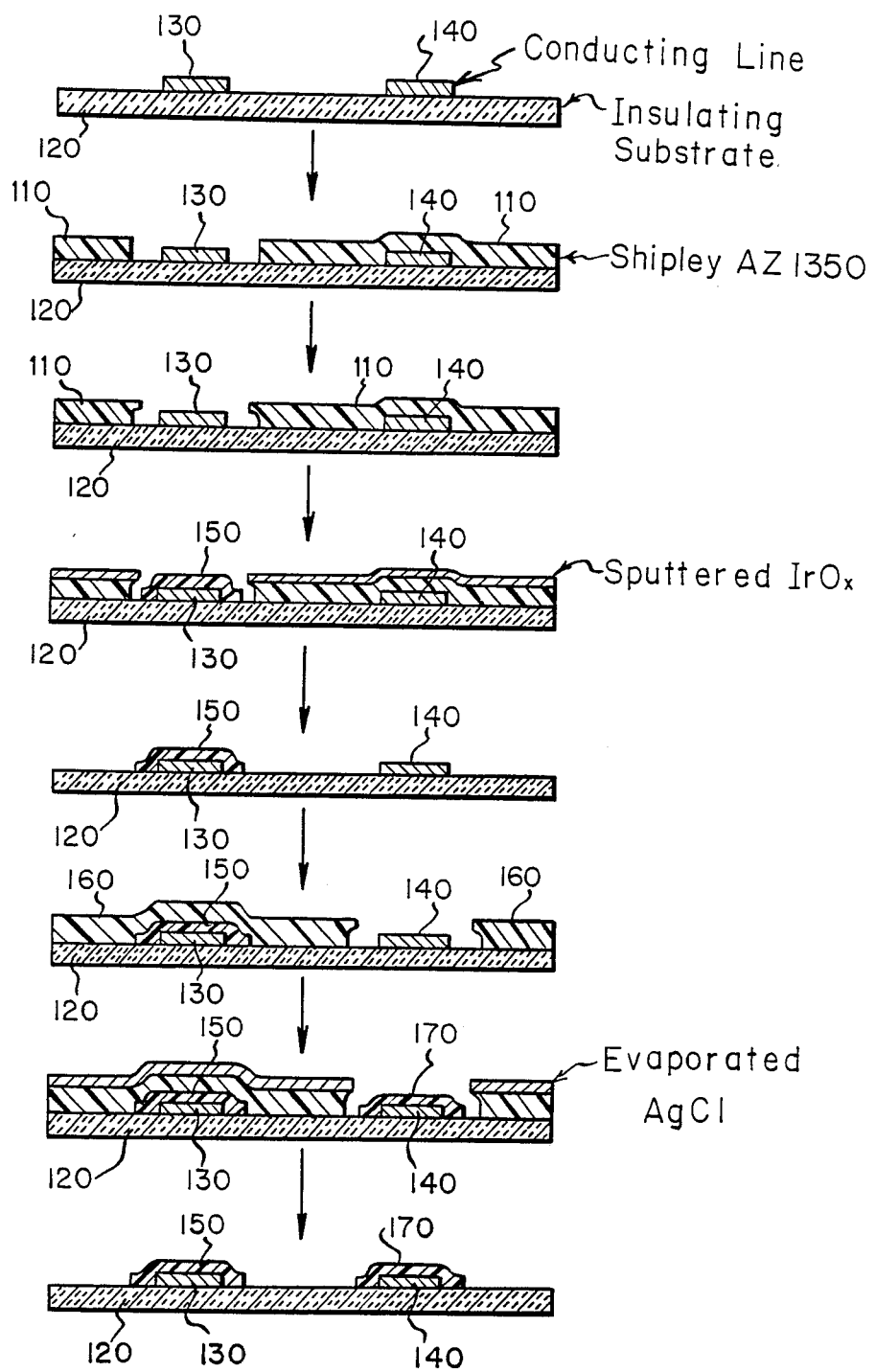
FIGS. 3 and 4 depict the formation of multi-element electrodes in accordance with my invention.

As shown in FIG. 3, two inorganic membranes sensitive to different chemical species may be deposited in vacuum on the same silicon substrate. In accordance with this technique, a photoresist layer 110 is first formed on a silicon substrate 120 on which there are conducting lines 130, 140. A window is then made in the photoresist for the formation of a first chemical sensitive layer 150. The substrate is then dipped in solvent to cause surface expansion of the photoresist so that the photoresist overhangs the edges of the window; and the first sensitive layer is then vacuum deposited on the substrate. The photoresist is then removed by a resist stripper, leaving bare the surface of the substrate except for a first region on which the first sensitive layer was deposited. A second photoresist layer 160 is then deposited and this layer is exposed and treated to form a window in the photoresist where a second sensitive layer 170 can be formed. The photoresist is then dipped in solvent to expand its surface and the second sensitive layer is then applied by vacuum deposition. By treating the resist in a resist stripper, the second sensitive layer can be removed from all portions of the device except that portion that was deposited in the window in the photoresist. This process can be repeated indefinitely to form still additional sensitive layers on the surface of the substrate.

The foregoing method can in general be used with vacuum deposited materials such as evaporated AgCl, $Ag_2S$, $LaF_3$; reactively sputtered $IrO_x$, $IrS_x$; and r.f. sputtered phosphates of Bi or Mn. As will be apparent, there is no contact between the different sensitive layers in the foregoing process. As a result there is no cross-contact of the sensitive layers. Moreover, since the sensitive layers are never exposed to any etching, their etch properties are irrelevant.

The problem of forming sensitive layers from polymers or hydrogels is more acute. These materials are deposited by spin-on or some related solvent casting technique. Therefore, it is vital that they do not come into contact at any stage. Consider for example, two different PVC doped membranes, one of which is PVC doped with valinomycin and plasticised with bis-2-ethyhexyladipate, and the other of which is PVC doped wth Ca salt or mono and di ester of octylphenyl phosphate and plasticised with octylphenyl phosphonate. Both films are spin-coated from tetrahydrofuran solution (THF) and therefore deposition of one will cause redissolving of the other if they contact. Furthermore, intermixing of the ionophore will cause loss of specificity.

Figure 4:
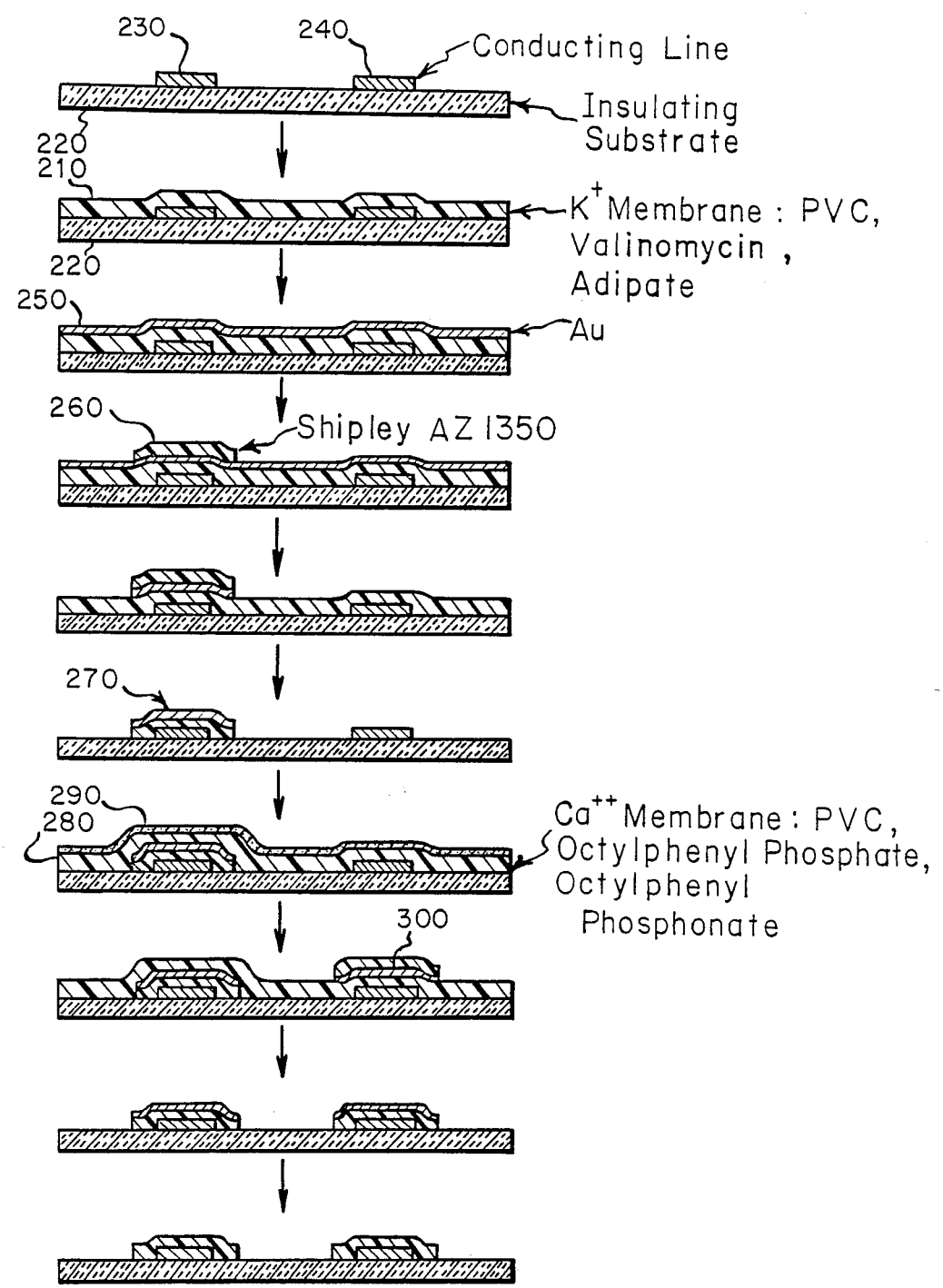

Situations such as these may be accommodated by a second embodiment of the invention. As shown in FIG. 4, a PVC film 210 sensitive to a first chemical is spin-coated on a substrate 220 on which there are conducting layers 230, 240. Film 210 is then overcoated with a thin inorganic material 250 by plasma deposition or by spinning or by evaporation in the case of a metal. This inorganic material serves to isolate the organic material from the photoresist that is subsequently used. The inorganic material may be a metal such as gold or an insulator such as $SiO_2$ or $Si_3N_4$. A layer of photoresist 260 is then deposited on the inorganic material and a pattern is defined photolithographically in the photoresist above a first region of the substrate. This pattern is then transferred by etching into the inorganic and PVC layers to form a first chemical sensitive device 270. After removal of the photoresist remaining above the inorganic material covering the first region, another PVC layer 280 sensitive to a second chemical can be deposited on the entire substrate including the inorganic material above the first region. This layer is then coated with an inorganic material 290. Another layer of photoresist 300 can then be deposited and shaped to form a second pattern on a second region of the substrate. This pattern can likewise be transferred to the inorganic material and the PVC layer by etching to form a second chemical sensitive device. The remaining photoresist can then be removed and the process repeated indefinitely to form still other chemical sensitive devices. Finally, the inorganic layers are removed leaving on the substrate as many different sensitive devices as were formed by the foregoing process.

For example, the first PVC film 210 might be PVC doped with valinomycin and the second PVC layer 180 might be PVC doped with the calcium salt of mono and di ester of octylphenyl phosphonate.

This same technique can be applied to the patterning of gel layers for Severinghaus electrodes. The materials to be patterned in this case would be, for example, polyvinylalcohol (PVA), polymethylmethacrylate (PMMA) and polyhydroxymethylmethacrylate (PHMMA) etc., gelatinized with $H_2O$ containing electrolyte salts, and deposited as thin film coatings.

Figure 5:
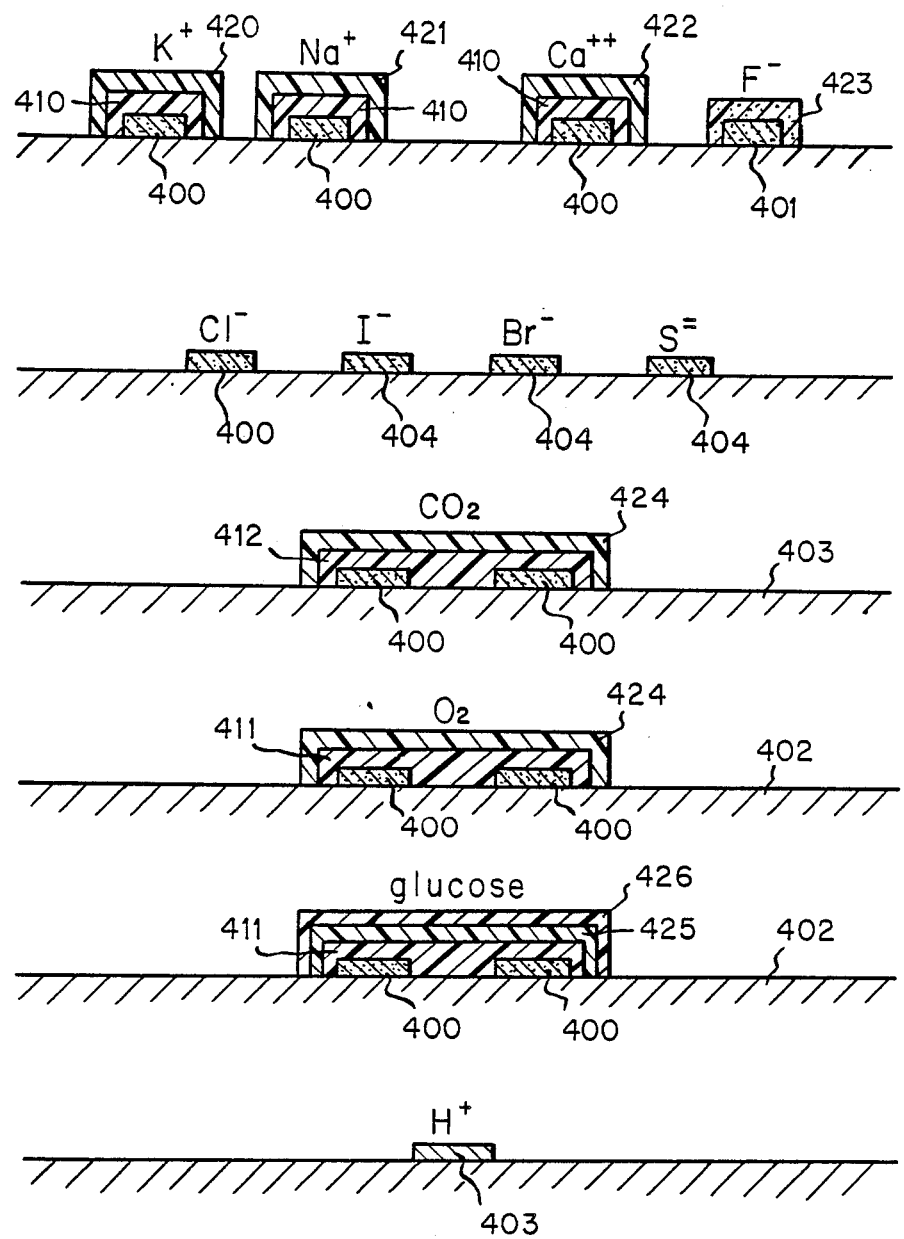
FIGS. 5 and 6 depict a twelve element electrode formed in accordance with the invention.
Figure 6:
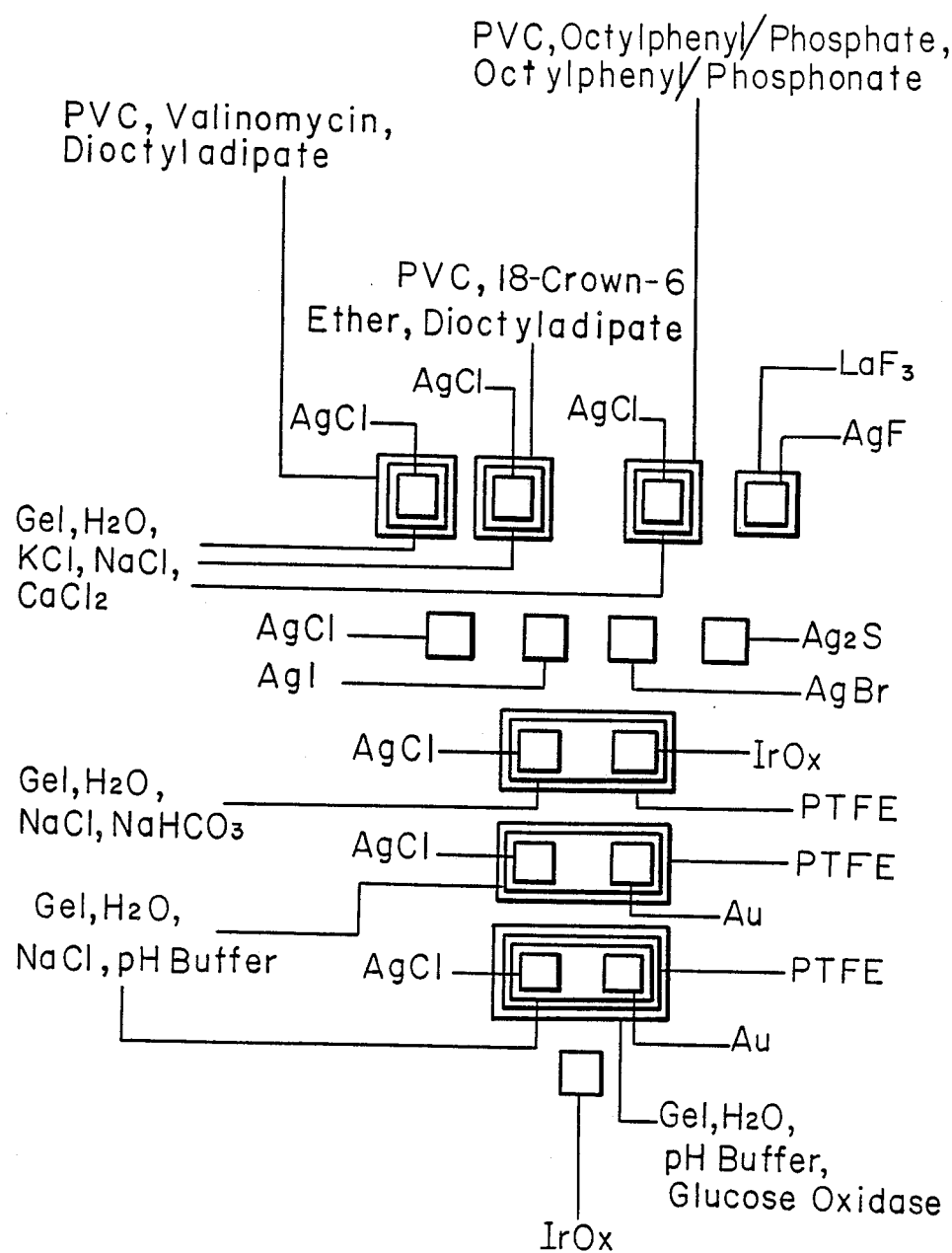

The technique described in FIGS. 3 and 4 may also be combined in the formation of a single electrode that is sensitive to several different ions of chemical parameters. For example, the layout of a device sensitive to $K^+$, $Na^+$, $Ca^{++}$, $F^-$, $Cl^-$, $I^-$, $Br^-$, $S^=$, $CO_2$, $O_2$, glucose and $H^+$ is illustrated in FIGS. 5 and 6. FIG. 5 depicts the cross sectional structure of the individual electrodes for sensing these 12 parameters and also indicates the relative location of each of these electrodes in the plan view of FIG. 6. FIG. 6 indicates illustrative orientation of these electrodes on a monolithic silicon substrate. As will be apparent AgCl is used as an innermost layer 400 of the electrodes that sense for $K^+$, $Na^+$, $Ca^{++}$ and $Cl^-$. It is also used as an innermost layer 400 in the reference electrodes in the sensors for $CO_2$, $O_2$ and glucose. AgF is used as an innermost layer 401 in the $F^-$ sensor, Au is used as an innermost layer 402 in the $O_2$ and glucose sensors, $IrO_x$ is used as an innermost layer 403 in the $CO_2$ sensor and the sole layer in the $H^+$ sensor; and AgI, AgBr, and $Ag_2S$ are used as the sole layers 404 in the $I^-$, $Br^-$ and $S^{--}$ electrodes.

An aqueous gel containing KCl, NaCl and $CaCl_2$ is used as an intermediate layer 410 in the $K^+$, $Na^+$ and $Ca^{++}$ electrodes; an aqueous gel containing NaCl and a pH buffer is used as an intermediate layer 411 in the $O_2$ and glucose electrodes and an aqueous gel containing NaCl and $NaHCO_3$ is used as an intermediate layer 412 in the $CO_2$ electrode.

The outer layer 420 of the $K^+$ electrode is made of PVC containing valinomycin and dioctyladipate; the outer layer 421 of the $Na^+$ electrode is made of PVC containing 18-crown-6 ether, dioctyladipate; and the outer layer 422 of the $Ca^{++}$ electrode is made of PVC containing octylphenylphosphate and octylphenylphosphonate. The outer layer 423 of the $F^-$ electrode is made of $LaF_3$. The outer layer 424 of the $CO_2$ and $O_2$ electrodes is made of PTFE. Two layers 425, 426 are required to complete the glucose electrode. The first layer 425 being made of PTFE and the outer layer 426 being an aqueous gel containing a pH buffer and glucose oxidase.

As indicated above, the metals, metal salts and iridium oxide may be deposited on the substrate following the steps outlined in connection with FIG. 3. After these are formed, the gels, PVC layers and PTFE may be deposited following the steps outlined in FIG. 4.

The foregoing techniques may also be combined with conventional photolithographic techniques to permit the integrated circuit fabrication of chemically sensitive layers and conventional transistor circuitry on a single monolithic semiconductor substrate. The concurrently filed application, "Extended Gate Field Effect Transistor," describes such a process for a field effect transistor in which the sensitive layer is formed on a signal line connected to the gate of the field effect transistor. If desired, the same process could also be used to form the sensitive layer directly on the gate of the field effect transistor.

Figure 7:
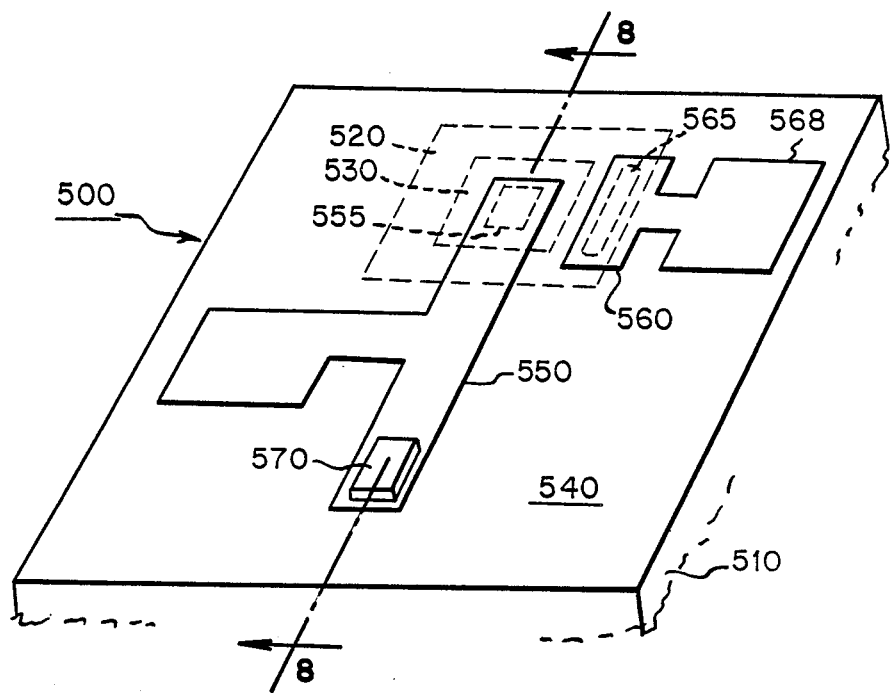
FIG. 7 is a view of a bipolar transistor and a chemically sensitive device of the present invention.
Figure 8:
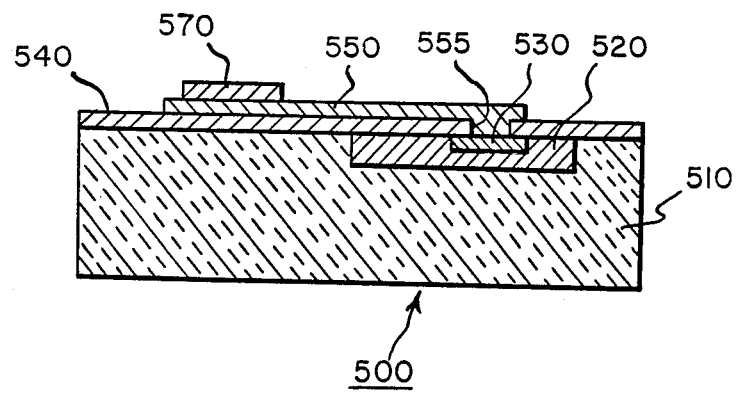
FIG. 8 is a cross-sectional view along lines 8-8 of the device of FIG. 7.

We have found that this same process can also be used to form a sensitive layer on the same substrate as a bipolar transistor or a junction field effect transistor. For example, as shown in FIGS. 7 and 8, a bipolar transistor 500 comprises a substrate and collector region 510 of one conductivity type in which there is formed a base region 520 of a second conductivity type in which there is formed an emitter region 530 of the first conductivity type. As is known in the art the first conductivity type could be either p or n and different concentrations of p or n can be used in the different regions. For convenience, the term substrate will be used generally to include the semiconductive portion of the transistor.

On the surface of the substrate is an insulating oxide layer 540 and on top of the oxide layer are conductive layers 550, 560. Layer 550 is in ohmic contact with emitter region 530 through a window 555 in the oxide; and layer 560 is in ohmic contact with base region 520 through a window 565 in the oxide. Bonding pad 568 is used to permit electrical connection to be made from other parts of the circuit to the base region. Alternatively, such connections could be made by conductive layers deposited on the surface of the insulating oxide as is known in the art.

A chemically sensitive layer 570 is formed on conductive layer 550 over a portion of the substrate removed from the emitter and base regions 520, 530. As a result, the chemically sensitive layer can be exposed to the ambient it measures without exposing the region above the emitter and base regions to such environment. As will be appreciated, this is especially useful where the environment contains ionic species which might migrate through the conductive layer and/or oxide and degrade the performance of the transistor.

Where the environment is not hostile, the chemically sensitive layer could be formed directly on the emitter region or on a metal layer directly above it, if desired.

Figure 9:
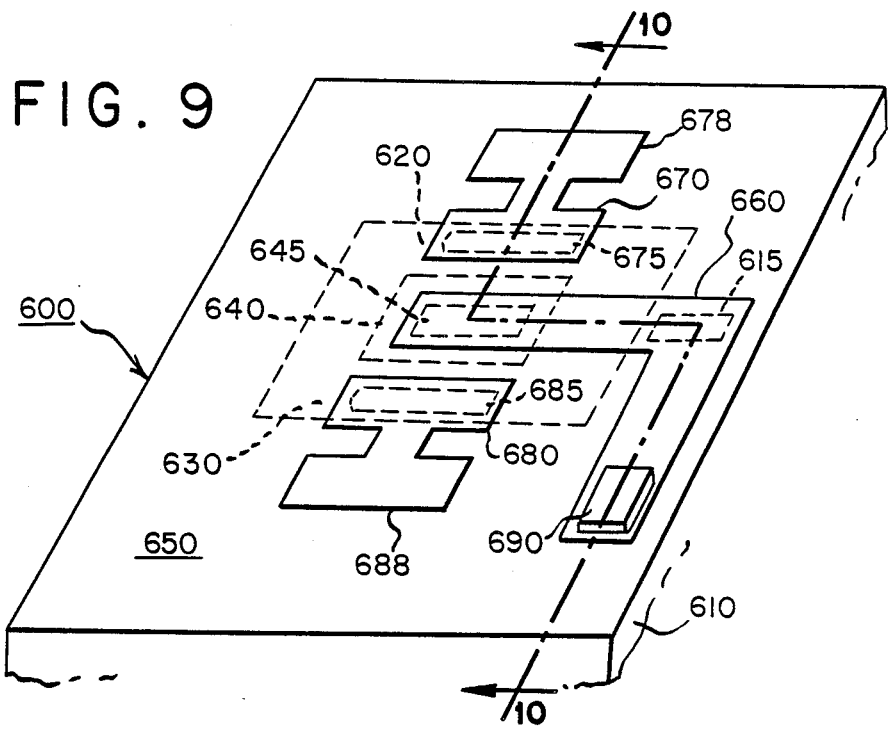
FIG. 9 is a view of a JFET and a chemically sensitive device of the present invention.
Figure 10:
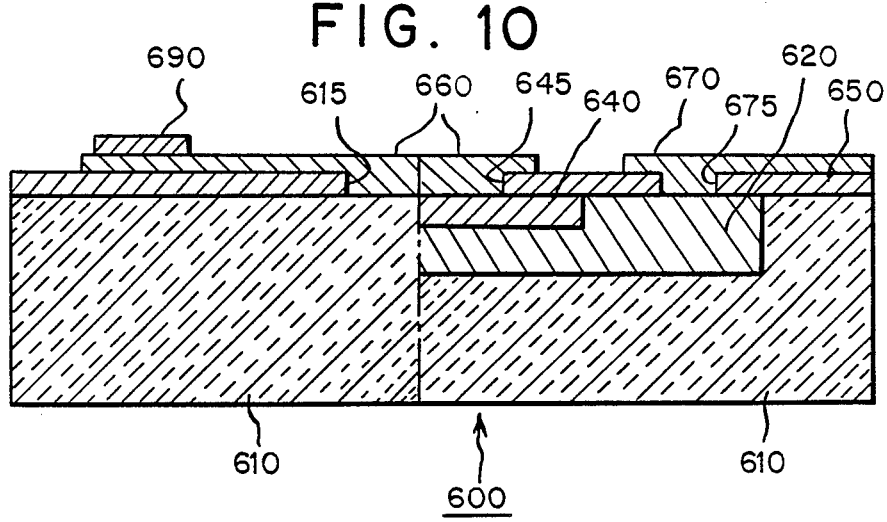
FIG. 10 is a cross-sectional view along lines 10—10 of the device of FIG. 9.

As shown in FIGS. 9 and 10, the same process may be implemented with a junction field effect transistor 600. Such device comprises a substrate 610 of one conductivity type in which are defined source and drain regions 620, 630 of a second conductivity type and a gate region 640 of the first conductivity type.

On the surface of the substrate is an insulating oxide layer 650 and on top of the oxide layer are conductive layers 660, 670 and 680. Layer 660 is in ohmic contact with gate region 640 through a window 645 and with substrate 610 through a window 615. Layers 670, 680 are in ohmic contact with source and drain regions 620, 630 respectively through windows 675, 685 respectively. Bonding pads 668, 678 and 688 or additional metallization provide electrical connections to other parts of the circuit.

As in the case of the extended gate field effect transistor, a chemically sensitive layer 690 is formed on conductive layer 660 over a portion of the substrate removed from the gate region. Alternatively layer 690 could be deposited directly on gate region 640 if the environment permitted.

Where the sensing device is located on a portion of the device removed from the gate region or emitter and base regions of the transistor, the sensing device is advantageously connected to the gate or emitter by a shielded coaxial line. As disclosed in the concurrently filed application, "Extended Gate Field Effect Transistor," this coaxial line may be formed of three conductive layers separated by oxide layers with the first and third layers electrically connected to form a shield about the second layer which serves as a signal line. The coaxial line is formed by successively depositing a first layer of conductor, a first oxide layer, a second layer of conductor, a second oxide layer and finally a third layer of conductor. The second layer of conductor has a lateral dimension that is smaller than the other two so that the second oxide layer encapsulates it. The connection between the first and third layers of conductor is made by opening windows in the second oxide layer to expose the first layer of conductor along both sides of the second layer of conductor and then depositing the third layer of conductor so that it contacts the first layer.

As will be apparent to those skilled in the art, numerous other combinations of these steps may be devised to prepare monolithic substrate electrodes that are sensitive to more than one chemical parameter.

When a coaxial line is used with a JFET connected as a source follower its shield may advantageously be connected to the source region of the JFET to provide bootstrapping.

Amperometric sensors may be realized by connecting the sensor to an on-chip operational amplifier used as a current to voltage converter. To produce an output proportional to the current generated at the chemical sensor, the feedback element $Z_f$ of the op-amp should be resistive. To provide a coulometric sensor the feedback element should be capacitive.

Amperometric sensors may also be realized with FET and bipolar transistors using common gate and common base configurations. Because the input impedance of a common base is equal to the inverse of the transconductance, the output impedance can be kept low. In a common gate circuit, the chemical sensor should be connected to the source region of the FET rather than the gate region as in the embodiment of FIGS. 9 and 10.

Figure 11:
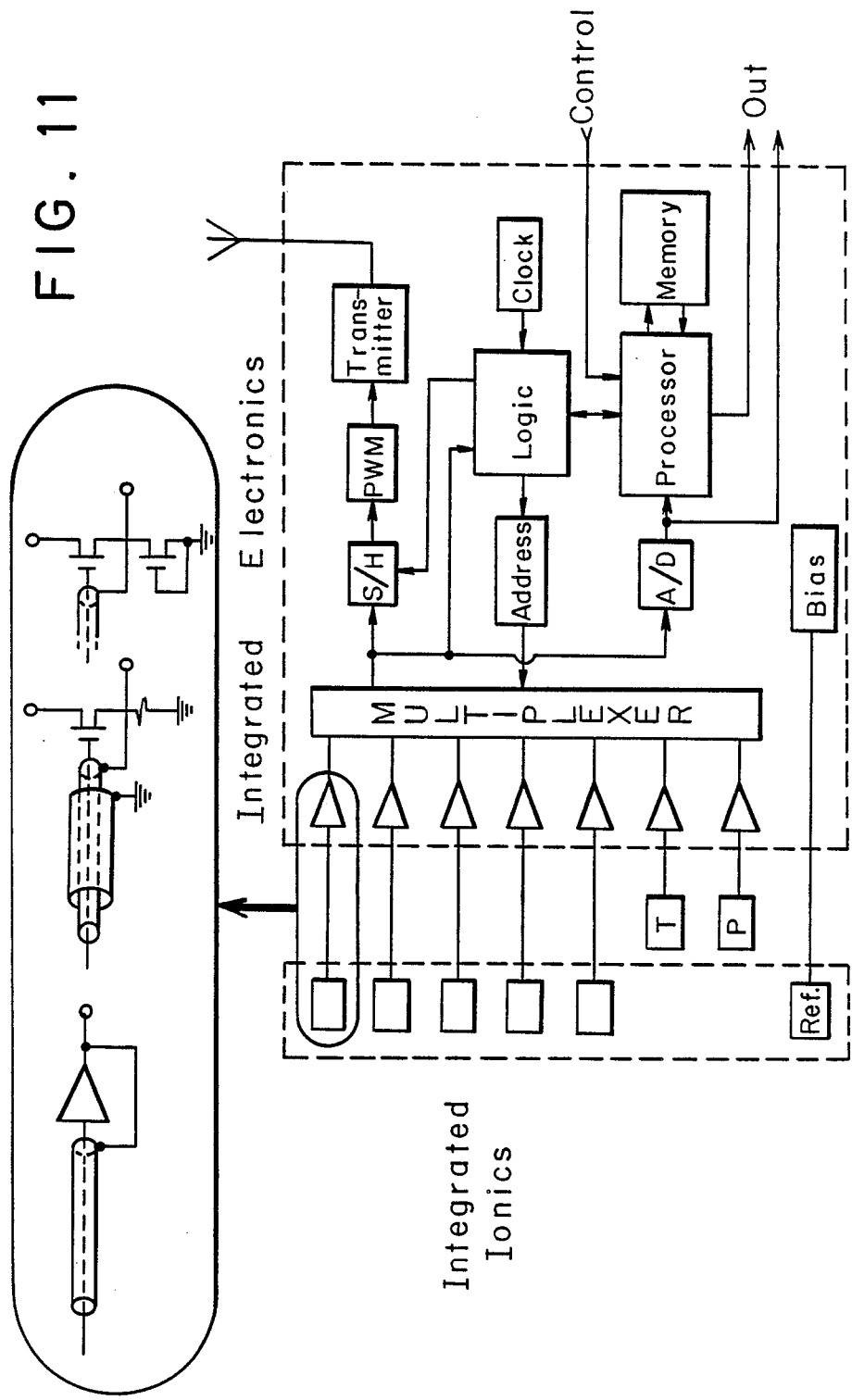
FIG. 11 is a block diagram of a multi-element sensor of the present invention.

A block diagram of a multi-element sensing device that may be integrated on a single silicon substrate is shown in FIG. 11. This device comprises five sensors for sensing five different chemical or ionic species, a reference electrode, pressure and temperature sensors. The electronics package is conventional and includes a multiplexer and a microprocessor for reading the sensors and transmitting output signals related thereto.

What is claimed is:

1. A multi-element ambient sensing probe comprising:
   a semiconductive substrate,
   a plurality of transistor devices defined by photolithographic techniques in said semiconductive substrate, each said transistor device including a control electrode,
   a first means for sensing at least one property of the ambient, said first means comprising a first sensitive material defined by photolithographic techniques on said substrate and in electrical connection with a first said control electrode, and
   a second means for sensing at least one property of the ambient different from that sensed by said first means, said second means comprising a second sensitive material defined by photolithographic techniques on said substrate and in electrical connection with a second said control electrode, wherein at least one of the first and second sensitive materials would dissolve the other if they came in contact.

2. The apparatus of claim 1 wherein the first sensing means is connected to said first control electrode by a first conductor formed on an insulating layer on said semiconductor substrate.

3. The apparatus of claim 2 wherein the first conductor comprises a signal line and a conductive shield.

4. The apparatus of claim 1 wherein the first and second transistor devices are field effect transistors and the control electrodes are gate electrodes.

5. The apparatus of claim 1 wherein the first and second transistor devices are bipolar transistors.

6. The apparatus of claim 1 wherein the first and second sensing means and the plurality of transistor devices are all formed on the same side of the semiconductive substrate.

7. The apparatus of claim 3 wherein the signal line and shield are formed photolithographically.

8. The apparatus of claim 7 wherein the signal line and shield are formed of polysilicon.

* * * * *